United States Patent [19]

Croop et al.

[11] Patent Number: 5,198,344
[45] Date of Patent: Mar. 30, 1993

[54] DNA SEQUENCE THAT ENCODES THE MULTIDRUG RESISTANCE GENE

[75] Inventors: James M. Croop, Jamaica Plain, Mass.; Philippe Gros, Montreal, Canada; David E. Housman, Newton, Mass.

[73] Assignee: Massachusetts Institute of Technology, Cambridge, Mass.

[21] Appl. No.: 652,311

[22] Filed: Feb. 6, 1991

Related U.S. Application Data

[63] Continuation of Ser. No. 885,951, Jul. 15, 1986, abandoned.

[51] Int. Cl.$^5$ .................. C12P 21/02; C12P 19/34; C12N 15/00; C12N 7/00; C12N 5/00; C07K 3/00; C07H 15/12

[52] U.S. Cl. .................. 435/69.1; 435/91; 435/172.3; 435/235.1; 435/320.1; 435/240.2; 536/23.5; 530/350; 935/18; 935/32; 935/42; 935/57; 935/61; 935/70; 935/71; 935/77

[58] Field of Search .................. 435/69.1, 91, 172.3, 435/235, 240.1, 320.1; 536/27; 530/380; 935/18, 32, 42, 57, 61, 70, 71, 77

[56] References Cited

PUBLICATIONS

Kaufman, R. et al Mol and Cellular Biol. vol. 2 pp. 1304–1319 (1982).

P. Gros, et al., *Proceedings of the National Academy of Science, USA*, 83: 337–341 (1986).

J. L. Biedler, et al., *Journal of Cellular Biochemistry, Abstracts, UCLA Symposia on Molecular and Cellular Biology*, A123 (15th Annual Meetings, Jan. 20–Feb. 15, 1986).

J. E. Byfield, *Journal of Cellular Biochemistry, Abstracts, UCLA Symposia on Molecular and Cellular Biology*, A124 (15th Annual Meetings, Jan. 20–Feb. 15, 1986).

D. F. Cano-Gauci and J. R. Riordan, *Journal of Cellular Biochemistry, Abstracts, UCLA Symposia on Molecular and Cellular Biology*, A125 (15th Annual Meetings, Jan. 20–Feb. 15, 1986).

I. Pastan, et al., *Journal of Cellular Biochemistry, Abstracts, UCLA Symposia on Molecular and Cellular Biology*, A13 (15th Annual Meetings, Jan. 20–Feb. 15, 1986).

C. Cillo, et al., *Journal of Cellular Biochemistry, Abstracts, UCLA Symposia on Molecular and Cellular Biology* (15th Annual Meetings, Jan. 20–Feb. 15, 1986).

D. P. Clark et al., *Journal of Cellular Biochemistry, Abstracts, UCLA Symposia on Molecular and Cellular Biology*, A130 (15th Annual Meetings, Jan. 20–Feb. 15, 1986).

M. M. Cornwell et al., *Journal of Cellular Biochemistry, Abstracts, UCLA Symposia on Molecular and Cellular Biology*, A131 (15th Annual Meetings, Jan. 20–Feb. 15, 1986).

K. Deuchards and V. Ling, *Journal of Cellular Biochemistry, Abstracts, UCLA Symposia on Molecular and Cellular Biology*, A133 (15th Annual Meetings, Jan. 20–Feb. 15, 1986).

R. L. Juliano and V. Ling, *Biochimica et Biophysica Acta*, 455:152–162 (1976).

J. R. Riordan and V. Ling, *The Journal of Biological Chemistry*, 254: 12701–12705 (1979).

N. Kartner et al., *Science*, 221:1285–1288 (1983).

(List continued on next page.)

*Primary Examiner*—Joan Ellis
*Attorney, Agent, or Firm*—Hamilton, Brook, Smith & Reynolds

[57] ABSTRACT

DNA homologous to mRNA expressed at significantly increased levels in drug-sensitive mammalian cells confers resistance to a variety of drugs on drug-sensitive mammalian cells when introduced into those cells. The nucleotide sequence of the DNA, which is one member of a small family of multidrug resistance (mdr) genes, is disclosed, as is the amino acid sequence of the encoded product. Methods of conferring a multidrug resistance phenotype on drug-sensitive mammalian cells, methods of detecting the occurrence of an mdr gene, and antibodies specific for proteins encoded by mdr DNA are also described.

5 Claims, 11 Drawing Sheets

PUBLICATIONS

I. B. Roninson et al., *Proceedings of the National Academy of Sciences*, USA, 83:4538-4542 (1986).

A. T. Fojo et al., *Proceedings of the National Academy of Sciences*, USA, 82:7661-7665 (1985).

A. M. Van der Bliek et al., *Molecular and Cellular Biology*, 6:1671-1678 (1986).

K. W. Scotto et al., *Science*, 232:751-755 (1986).

J. M. Croop et al., *Journal of Cellular Biochemistry, Abstracts, Supplement 9c, UCLA Symposia on Molecular and Cellular Biology*, #1167 (14th Annual Meetings, Apr. 6-25, 1985).

I. B. Roninson et al., *Nature*, 309: 626-628 (1984).

J. R. Riordan et al., *Nature*, 316: 817-819 (1985).

N. Kartner et al., *Nature*, 316: 820-823 (1985).

Gros, P. et al., *Molecular and Cellular Biology*, 6:3785-3790 (Nov. 1986).

Deuchars, K. L. et al., *Molecular and Cellular Biology*, 7:718-724 (1987).

Shen, E. W. et al., *Molecular and Cellular Biology*, 6:4039-4044 (Nov. 1986).

Gros, P. et al., *Nature*, 323:728-731 (Oct. 1986).

Gros, P. et al., *Cell*, 47:371-380 (Nov. 1961).

Chen, C. J. et al., *Cell*, 47:381-389 (Nov. 1986).

Gerlach, J. H. et al., *Nature*, 324:485-489 (Dec. 1986).

Ueda, K. et al., *Journal of Biological Chemistry*, 262:505-508 (1987).

Ueda, K. et al., *Proc. National Academy of Sciences*, USA, 84:3004-3008 (1987).

Thorgeirsson, S. S. et al., *Science*, 236:1120-1122 (May 1987).

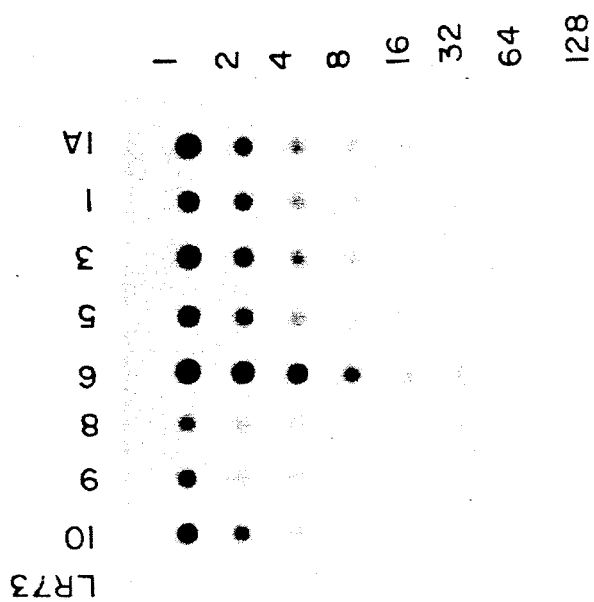
FIG. 7c
FIG. 7b
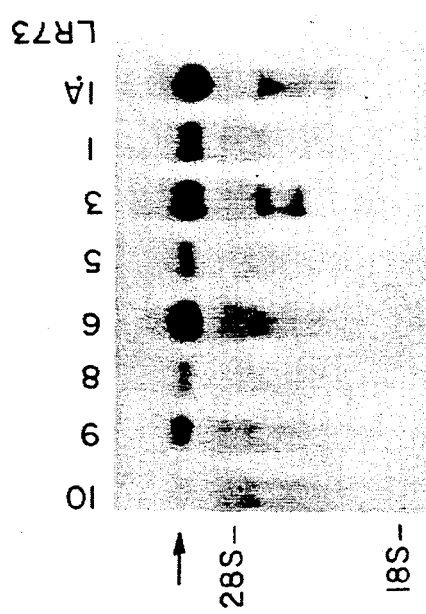
FIG. 7a

FIGURE 8 A

GAGGCGCTGCTTCCATCTTCTGAGGTTCCGCTCAACTCAGAGCTACTTCCAAATTCTACATCTTG
GCTGACTTTGCGAAGGAAACCCGGAGGTGGCACGTGAGGTGGTGATGGAGTTTGAAGAGAACCTT
AAGGGAAGAGCAGACAAGAACTTCTCGAAGATGGGCAAAAAGAGTAAAAAGGAGAAGAAAGAAAA
GAAACCTGCTGTTGGCGTATTTGGGATGTTTCGCTATGCAGATTGGCTGGACAAGCTGTGCATGA
TTCTGGGAACTCTCGCTGCTATTATCCATGGAACATTACTTCCCCTCTTGATGCTGGTGTTTGGA
AACATGACAGATAGTTTTACAAAAGCAGAAGCCAGTATTCTGCCAAGCATTACTAATCAAAGTGG
ACCCAACAGTACTCTGATCATCAGCAACAGCAGTCTGGAGGAAGAGATGGCCATATACGCCTACT
ATTACACCGGGATTGGTGCTGGTGTGCTCATAGTTGCCTACATCCAGGTTTCACTTTGGTGCCTG
GCAGCTGGAAGACAGATACACAAGATTAGGCAGAAGTTTTTCCATGCTATAATGAATCAGGAGAT
AGGCTGGTTTGATGTGCATGATGTTGGGGAGCTCAACACCCGGCTCACAGATGATGTCTCCAAAA
TTAATGACGGAATTGGTGACAAAATTGGGATGTTTTTTCAGTCCATAACCACATTTTTAGCCGGT
TTTATCATAGGATTTATAAGTGGTTGGAAGCTAACCCTTGTCATTTTGGCTGTCAGCCCTCTTAT
TGGATTGTCATCTGCTTTGTGGGCAAAGGTATTGACTTCATTTACTAATAAGGAACTCCAGGCTT
ATGCAAAAGCTGGAGCAGTTGCTGAAGAAGTCTTAGCAGCCATCAGAACTGTGATTGCCTTTGGA
GGACAACAGAAGGAACTTGAAAGGTACAATAAAAATTTAGAAGAAGCTAAAAATGTTGGCATAAA
GAAAGCTATCACAGCCAGCATTTCGATAGGCATTGCCTACCTGTTGGTCTATGCATCATATGCAC
TGGCATTCTGGTATGGGACATCCTTGGTCCTCTCAAATGAATATTCTATTGGAGAAGTGCTTACT
GTCTTCTTCTCTATTTTGTTGGGGACTTTTAGTATTGGACACTTGGCCCCAAACATAGAAGCCTT
TGCAAACGCACGAGGGGCAGCCTTTGAAATCTTCAAGATAATTGATAACGAGCCAAGCATTGACA
GCTTCTCAACAAAGGGCTACAAACCAGACAGTATAATGGGAAACTTAGAGTTTAAAAATGTTCAC
TTCAACTACCCATCGAGAAGCGAAGTTCAGATCTTGAAGGGCCTCAATCTGAAGGTGAAGAGCGG
ACAGACGGTGGCCTTGGTTGGCAACAGTGGCTGTGGAAAAAGCACAACTGTCCAGCTGATGCAGA
GGCTCTACGACCCCCTGGAGGGCGTGGTCAGTATCGACGGACAAGACATCAGAACCATCAATGTG
AGGTATCTGAGGGAGATCATTGGTGTGGTGAGTCAGGAACCTGTGCTGTTTGCCACCACGATCGC
CGAGAACATTCGCTATGGCCGAGAAGATGTCACCATGGATGAGATTGAGAAAGCTGTCAAGGAAG

FIGURE 8 B

CCAATGCCTATGACTTCATCATGAAACTGCCCCACCAATTTGACACCCTGGTTGGTGAGAGAGGG
GCGCAGCTGAGTGGGGGACAGAAACAGAGAATCGCCATTGCCCGGGCCCTGGTCCGCAATCCCAA
GATCCTTTTGTTGGACGAGGCCACCTCAGCCCTGGATACAGAAAGTGAAGCTGTGGTGCAGGCCG
CACTGGATAAGGCTAGAGAAGGCCGGACCACCATTGTGATAGCTCATCGCTTGTCTACAGTTCGT
AATGCTGACGTCATTGCTGGTTTTGATGGTGGTGTCATTGTGGAGCAAGGAAATCATGATGAGCT
CATGAGAGAAAGGGCATTTACTTCAAACTTGTCATGACACAGACTAGAGGAAATGAAATTGAAC
CAGGAAATAATGCTTATGGATCCCAGAGTGACACTGATGCTTCTGAACTGACTTCAGAAGAATCC
AAATCACCTTTAATAAGGAGATCAATTTACAGAAGTGTCCACAGAAAGCAAGACCAAGAGAGAAG
ACTTAGTATGAAAGAGGCTGTGGATGAAGATGTGCCTCTGGTTTCCTTTTGGCGGATCCTAAATC
TAAATCTAAGTGAATGGCCTTATTTACTTGTTGGCGTACTTTGCGCTGTTATAAATGGGTGCATA
CAACCAGTGTTTGCCATAGTATTTTCAAGGATTGTAGGGGTTTTTTCAAGAGATGATGACCATGA
AACTAAACGACAGAATTGTAATTTGTTTTCCCTGTTCTTTCTGGTTATGGGCTGATTTCTTTTG
TTACATATTTCTTTCAGGGCTTCACATTTGGCAAAGCCGGAGAGATCCTCACCAAGCGAGTCCGA
TACATGGTTTTCAAATCCATGCTGAGACAGGATATAAGCTGGTTCGATGACCATAAGAACAGCAC
TGGCTCACTGACCACCAGGCTCGCCAGTGATGCTTCTAGTGTTAAAGGGGCGATGGGCGCCAGGC
TTGCTGTAGTTACCCAGAATGTAGCAAACCTCGGGACAGGAGTCATCCTCTCCTTAGTCTATGGC
TGGCAGCTGACACTTCTACTTGTAGTAATTATACCGCTCATTGTATTGGGCGGAATTATTGAAAT
GAAGCTGTTGTCTGGCCAAGCCTTGAAGGACAAGAAACAGCTTGAGATCTCTGGGAAGATTGCTA
CAGAAGCAATTGAAAACTTCCGCACTATTGTCTCTTTGACTCGGGAGCAGAAGTTTGAAACCATG
TATGCCCAGAGCTTGCAGGTACCATACAGAAATGCGATGAAGAAAGCACACGTGTTTGGGATCAC
GTTCTCCTTCACCCAGGCCATGATGTATTTTTCTTATGCTGCTTGTTTCCGGTTCGGTGCCTACT
TGGTGGCACAACAACTCATGACTTTTGAAAATGTTATGTTGGTATTTTCTGCTGTTGTCTTTGGT
GCCATGGCAGCTGGGAATACTAGTTCATTTGCTCCTGACTATGCGAAAGCCAAAGTATCAGCATC
TCATATCATCAGGATCATTGAGAAAACCCCTGAGATTGACAGCTACAGCACAGAGGGCTTGAAGC
CTACTCTGTTAGAAGGAAATGTAAAATTTAATGGAGTCCAGTTTAACTATCCCACCCGACCCAAC

FIGURE 8 C

ATCCCAGTGCTTCAGGGGCTGAGCCTCGAGGTGAAGAAGGGCCAGACGTTGGCCCTGGTGGGCAG
CAGTGGCTGTGGGAAGAGCACAGTGGTCCAGCTGCTCGAGCGCTTCTACGACCCCATGGCTGGAT
CAGTGTTTCTAGATGGCAAAGAAATAAAGCAACTGAATGTCCAGTGGCTCCGAGCTCACCTTGGC
ATTGTGTCCCAGGAGCCCATTCTCTTTGACTGCAGCATTGCAGAGAACATCGCCTATGGAGACAA
CAGCCGGGCCGTGTCTCATGAGGAGATTGTGAGGGCAGCCAAGGAGGCCAACATCCACCAGTTCA
TCGACTCACTGCCTGATAAATACAACACCAGAGTAGGAGACAAAGGCACTCAGCTGTCGGGTGGG
CAGAAGCAGCGCATCGCCATCGCACGTGCCCTCGTCAGACAGCCTCACATTTTACTTCTGGACGA
AGCAACATCAGCTCTGGATACAGAAAGTGAAAAGGTTGTCCAGGAAGCGCTGGACAAAGCCAGGG
AAGGCCGCACCTGCATTGTGATCGCTCACCGCCTGTCCACCATCCAGAACGCGGACTTGATCGTG
GTGATTGAGAACGGCAAAGTCAAGGAGCACGGCACCCACCAGCAGCTGCTGGCGCAGAAGGGCAT
CTACTTCTCAATGGTCCAGGCTGGAGCAAAGCGCTCATGAGCTGTGACTATCTGAGGTGCTAAGT
ATTTTTAATATTGGTGTTTAAACATGGCACCAAACCAAAGTTAAAAGGCAAGGGCTGTTAAAGGT
AACTCCATCAAGATGAGAAGCCTTCCGAGACTTTGTAATTAAATGAACCAAAATCGGAAACAAAC
AAACAAACAAACAAGCCATAGTTAAACAGCGCCATGTTTTAATTGCATTACGTGATTCAT
AAGAGAACATATAGTTTTTTAAAATAAAATGTATAATTTTGTTTCAGTTTTTAATTTCTACCCTA
CTTTCTTAAATGATTATAAAGATTGTAAAAAGCACTATTTCTTAAATTGCCTATAAAAATTAAAT
TTTCATATAAAAAAAAAAAAAAA

FIGURE 9

```
MEFEENLKGR ADKNFSKMGK KSKKEKKEKK PAVGVFGMFR YADWLDKLCM
ILGTLAAIIH GTLLPLLMLV FGNMTDSFTK AEASILPSIT NQSGPNSTLI
ISNSSLEEEM AIYAYYTGI GAGVLIVAYI QVSLWCLAAG RQIHKIRQKF
FHAIMNQEIG WFDVHDVGEL NTRLTDDVSK INDGIGDKIG MFFQSITTFL
AGFIIGFISG WKLTLVILAV SPLIGLSSAL WAKVLTSFTN KELQAYAKAG
AVAEEVLAAI RTVIAFGGQQ KELERYNKNL EEAKNVGIKK AITASISIGI
AYLLVYASYA LAFWYGTSLV LSNEYSIGEV LTVFFSILLG TFSIGHLAPN
IEAFANARGA AFEIFKIIDN EPSIDSFSTK GYKPDSIMGN LEFKNVHFNY
PSRSEVQILK GLNLKVKSGQ TVALVGNSGC GKSTTVQLMQ RLYDPLEGVV
SIDGQDIRTI NVRYLREIIG VVSQEPVLFA TTIAENIRYG REDVTMDEIE
KAVKEANAYD FIMKLPHQFD TLVGERGAQL SGGQKQRIAI ARALVRNPKI
LLLDEATSAL DTESEAVVQA ALDKAREGRT TIVIAHRLST VRNADVIAGF
DGGVIVEQGN HDELMREKGI YFKLVMTQTR GNEIEPGNNA YGSQSDTDAS
ELTSEESKSP LIRRSIYRSV HRKQDQERRL SMKEAVDEDV PLVSFWRILN
LNLSEWPYLL VGVLCAVING CIQPVFAIVF SRIVGVFSRD DDHETKRQNC
NLFSLFFLVM GLISFVTYFF QGFTFGKAGE ILTKRVRYMV FKSMLRQDIS
WFDDHKNSTG SLTTRLASDA SSVKGAMGAR LAVVTQNVAN LGTGVILSLV
YGWQLTLLLV VIIPLIVLGG IIEMKLLSGQ ALKDKKQLEI SGKIATEAIE
NFRTIVSLTR EQKFETMYAQ SLQVPYRNAM KKAHVFGITF SFTQAMMYFS
YAACFRFGAY LVAQQLMTFE NVMLVFSAVV FGAMAAGNTS SFAPDYAKAK
VSASHIIRII EKTPEIDSYS TEGLKPTLLE GNVKFNGVQF NYPTRPNIPV
LQGLSLEVKK GQTLALVGSS GCGKSTVVQL LERFYDPMAG SVFLDGKEIK
QLNVQWLRAH LGIVSQEPIL FDCSIAENIA YGDNSRAVSH EEIVRAAKEA
NIHQFIDSLP DKYNTRVGDK GTQLSGGQKQ RIAIARALVR QPHILLLDEA
TSALDTESEK VVQEALDKAR EGRTCIVIAH RLSTIQNADL IVVIENGKVK
EHGTHQQLLA QKGIYFSMVQ AGAKRS*
```

DNA SEQUENCE THAT ENCODES THE MULTIDRUG RESISTANCE GENE

SPONSORSHIP

The invention described herein was supported by a grant from the Medical Research Council of Canada, grants from the National Institutes of Health and a grant from the Ajinomoto Corporation.

This is a continuation of co-pending application Ser. No. 06/885,951 filed on Jul. 15, 1986, abandoned.

BACKGROUND

Recent progress in the development of new cytotoxic drugs and improved treatment protocols have made chemotherapy successful in the treatment of various types of human cancers. However, there are important limitations to this method of treatment. For example, the chemotherapeutic agents exhibit both acute and cumulative toxicity for normal (i.e., noncancerous) tissues such as the heart, kidneys and bone marrow. The development of more selective therapeutic drugs and improved methods of delivery should help alleviate this problem. An equally significant limitation to the use of chemotherapy is the emergence and outgrowth of drug resistant cells. This problem is a particularly difficult one because tumor cells often become resistant to a broad spectrum of structurally and functionally unrelated drugs to which they have not been previously exposed. It is unlikely that this problem will be solved by the development of new drugs using presently available methods, however, because such cells are likely to exhibit crossresistance to these new agents. This phenomenon of resistance to multiple drugs has been termed multidrug resistance.

The basis for the development of resistance to a broad spectrum of drugs by cells is inherently difficult to study in vivo because of the heterogenous nature of the cell populations present in tumor specimens. In vitro models have been developed to study this phenomenom. Cultured rodent and human cells highly resistant to multiple cytotoxic drugs have been obtained by cultivating these cells in increasing concentrations of a single drug. Such cell lines have proven very useful in the study of the molecular parameters underlying multidrug resistance. For example, multidrug resistant cells (i.e., cells which exhibit resistance to a broad spectrum of drugs) have been shown to contain double minute chromosomes or homogeneously staining chromosomal regions, which suggests gene amplification contributes to multidrug resistance. Specifically, adriamycin- and colchicine-resistant hamster cells have been shown to contain amplified DNA fragments, some of which are amplified in both types of cells. A small segment of one of these commonly amplified fragments has been cloned by Roninson and co-workers and its degree of amplification has been shown to correlate with the degree of drug resistance. Roninson, I. B. et al., *Nature*, 309: 626–629. It has been suggested that decreased intracellular drug accumulation resulting from alterations in the plasma membrane is the mechanism by which multidrug resistance occurs. Ling, V. et al.: *Cancer Treatment Report*, 67:869–875 (1983); Inaba, M. et al.: *Cancer Research*, 39:2200–2206 (1979); Ling, V. and L.H. Thompson: *Journal of Cell Physiology*, 83:103–111 (1974). It has also been postulated that a plasma membrane glycoprotein of relative molecular mass 170,000 (designated P-glycoprotein), consistently found in multidrug resistant cell lines and transplantable tumors, in some way mediates multidrug resistance. Riordan, J.R. et al.: *Nature*, 316:817–819 (1985). In spite of considerable interest in and study of multidrug resistance, however, its basis remains unknown.

DISCLOSURE OF THE INVENTION

The present invention relates to the determination that resistance to a wide variety of drugs unrelated in structure and function is conferred on drug-sensitive mammalian cells by the introduction into those cells of DNA homologous to mRNA expressed at significantly increased levels in drug-resistant mammalian cells. It has been demonstrated that introduction into drug-sensitive mammalian cells of a member of a group of related genes (i.e., those which are complementary to mRNA(s) expressed at significantly increased levels in multidrug resistant cells) confers a multidrug resistance phenotype on the drug-sensitive cells. This group of genes and their cellular mRNA transcripts are designated mdr. That is, introduction of DNA homologous to mRNA(s) expressed at significantly increased levels in multidrug resistant cells has been shown to confer a multidrug resistance phenotype on such cells. In particular, it has been shown that drug-sensitive mammalian cells become resistant to a wide variety of drugs upon introduction into the cells of a 4.3 Kb DNA fragment homologous to mRNA(s) shown to be expressed at significantly increased levels in multidrug resistant LZ hamster cells.

The sequence of the 4.3 Kb DNA whose introduction into drug-sensitive mammalian cells confers multidrug resistance is disclosed, as is the deduced amino acid sequence of the encoded gene product. Methods of conferring a multidrug resistance phenotype on drug-sensitive mammalian cells and methods of detecting the occurrence of an mdr gene or DNA fragment, using DNA homologous to a mRNA expressed at increased levels in multidrug resistant cells, are described. Antibodies specific for proteins encoded by mdr DNA are also described, as are methods for their use in detecting in mammalian cells the presence of mdr DNA-encoded protein.

BRIEF DESCRIPTION OF THE DRAWINGS

FIGS 5a–h show colony formation by clones transfected with pDREX4 and cultured in medium containing one of three drugs.

FIGS. 7a, 7b, and 7c are blots showing the results of transcription analysis of cells transfected with pDREX4.

FIGS. 8A, 8B, and 8C are the nucleotide sequence of the mdr gene contained in clone lambda DR11.

FIG. 9 is the deduced amino acid sequence of the product encoded by the mdr gene of clone lambda DR11.

DETAILED DESCRIPTION OF THE INVENTION

Figure 1:
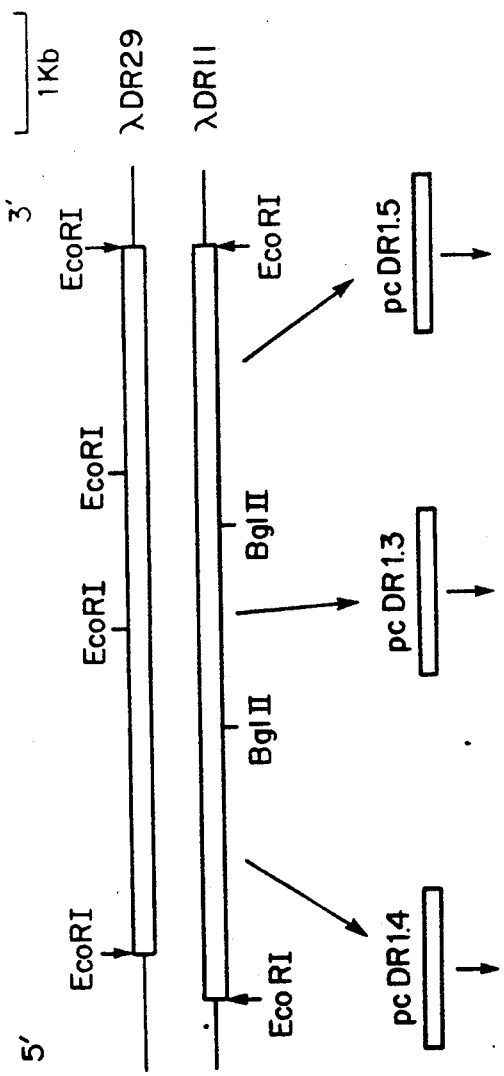
FIG. 1 is a schematic representation of the two longest lambda phage cDNA inserts, which are representative of the two independent populations of clones isolated from the mouse cDNA library.

Considerable effort has been made to elucidate the basis of multidrug resistance, particularly through use in the last decade of in vitro models. It appears that gene amplification at least in part underlies multidrug resistance and it has been suggested that DNA amplified in two independently derived multidrug-resistant Chinese hamster cell lines encodes a mRNA species (about 5 Kb in size) whose intracellular concentration correlates with the relative level of multidrug resistance in the cell lines. Gros, P. et al.: *Proceedings of the National Academy of Sciences, U.S.A.*, 83:337–341 (1986). In addition, detailed analysis of changes in the profile of cellular and membrane proteins in multidrug-resistant cells has resulted in the identification of several polypeptides (e.g., p21, p19, p70, p72, and gp170) which might play a role in mediating the resistance phenotype. Biedler, J. L. et al.: *Cancer Treatment Report*, 67: 859–868 (1983). Beck, W. T. et al.: *Cancer Research*, 39: 2070–2076 (1979). Kuo, T. et al.: *Gene Amplification* (ed. Schimke, R. T.), Cold Spring Harbor Laboratory, Cold Spring Harbor, N.Y., 53–62. Richerts, N. et al.: *Proceedings of the National Academy of Sciences, U.S.A.*, 82: 2330–2334 (1985). Ling, V. and Thompson, L. H. *Journal of Cellular Physiology*, 83: 103–111 (1974). Kartner, N. et al.: *Science*, 221: 1285–1289 (1983).

The technique of in gel renaturation has previously been used to identify and clone a DNA segment amplified in multidrug resistant cell lines. Two independently derived multidrug resistant hamster cell lines, LZ and C5, were shown to have amplified a common portion of their genome and a 1.1 Kb BamHI fragment from this commonly amplified domain was cloned. Chromosome walking techniques and in gel renaturation were subsequently used to clone and characterize a contiguous domain of 140 Kb of this amplified unit. Gros, P. et al.: *Proceedings of the National Academy of Sciences, U.S.A.*, 83:337–341 (1986). In addition, human and mouse homologs to the cloned hamster genes have been shown to be amplified and overexpressed in a series of resistant mouse lines and transplantable tumor cell lines, as well as in resistant human KB carcinoma lines. Gros, P. et al.: *Journal of Cellular Biochemistry*, 51: Abstract 10A, (1986); Fojo, A. T. et al.: *Proceedings of the National Academy of Sciences, U.S.A.*, 82:7661–7664 (1985). This group of genes and their cellular mRNA transcripts are referred to here by the designation mdr.

It has now been discovered that when one member of the mdr gene family is introduced into drug-sensitive mammalian cells, a drug-resistance phenotype is conferred upon those cells with the result that they exhibit resistance to drugs which are unrelated both structurally and functionally. When the mdr gene is expressed at a significantly increased level, previously drug-sensitive cells become multidrug resistant; that is, the mdr gene is expressed at levels which are higher than the level at which it is normally expressed and sufficiently elevated to produce the observed change in cell phenotype.

It has been shown that when a 4.3 Kb DNA fragment homologous to a mRNA expressed at increased levels in a variety of cells resistant to chemotherapeutic drugs is transfected into drug sensitive cells under conditions that allow high levels of transcription, the sensitive cells become resistant to a wide variety of chemotherapeutic agents which are unrelated in structure or mode of action; that is, the cells become multidrug resistant. The 4.3 Kb DNA fragment can efficiently confer a multidrug resistance phenotype upon transfection and encodes a gene product which, when expressed at significantly increased levels, is causally related to the development of multidrug resistance. The exact nature of the encoded gene product is still unclear; the mature polypeptide is likely, however, to be a membrane protein or membrane glycoprotein.

This information is the result of work which has focused on determining:
1) whether a causal relationship exists between increased expression of the mRNA(s) and emergence of multidrug resistance;
2) whether increased expression of a single member of the mdr group is sufficient to produce a drug resistance phenotype; and
3) whether multidrug resistance can be achieved by increased expression of an unaltered mdr gene (as opposed to a mutant form of the gene).

This has been accomplished through the approach described below in considerable detail.

The following is an overview of that approach: A cDNA library was constructed from mRNA which had been isolated from a drug-sensitive mouse cell line. Two mouse cDNA molecules complementary to the mRNA species encoded by two related but distinct mdr genes were isolated and cloned. One of these cDNA clones (lambda DR11) is a full length cDNA clone for one member of the mdr gene family. It was engineered in a mammalian expression vector (p91023B) which uses viral promoter/enhancer combinations to allow high levels of transcription of the cDNA upon introduction of the clone into mammalian cells. A eukaryotic expression vector was used and is described herein. It is possible, however, to use a prokaryotic expression vector having the desired characteristics (e.g., those which allow high levels of transcription) of the mdr gene. The mdr clone engineered in this way (pDREX4) was shown to confer the full multidrug resistance phenotype upon transfection into drug-sensitive mammalian cells. The cDNA thus encodes a gene product which, when expressed at increased levels, appears to be causally related to the phenomenon of multidrug resistance. As a result, it is evident that significantly increased expression of the normal gene of one member of the mdr gene family is sufficient to confer multidrug resistance on drug-sensitive cells. It is anticipated that expression at significantly increased levels of normal genes of other members of the mdr gene family can also confer multidrug resistance upon introduction into drug-sensitive cells. That is (referring to the three points outlined above), it has been determined that:
1) there is in fact a causal relationship between increased expression of the mRNA and multidrug resistance;
2) significantly increased expression of one member of the mdr gene family is necessary and sufficient to produce a drug resistance phenotype; and 3) multidrug resistance can be the result of overexpression of an unaltered (normal) mdr gene.

The sequence of the mdr gene contained in the full length cDNA clone has been determined and the amino acid sequence of the polypeptide it encodes deduced from it.

Isolation of mdr cDNA clones

To assess the role of mdr gene(s) in establishing multidrug resistance, a drug-sensitive mouse cell line was used to construct DNA clones complementary to the mdr mRNA(s); this mRNA is designated mdr mRNA(s). Previous work had shown that hamster, mouse and human mdr RNA(s) are between 4.5 Kb and 5 Kb in size.

To enrich for sequences in this size range, a size selection step was introduced into the cDNA cloning protocol; only cDNA inserts larger than 2.3 Kb were cloned in lambda phage gtll. Detailed experimental procedures for the construction of the library are described in Example 1.

Two genomic probes, pDR 7.8 and pDR 1.6, derived from the cloned mdr region amplified in multidrug resistant LZ hamster cells, were used to screen the cDNA library. Gros, P. et al., *Proceedings of the National Academy of Sciences, U.S.A.*, 83:337-341 (1986), the teachings of which are incorporated herein by reference. These two subclones were chosen because they were known to hybridize to the hamster mdr mRNA(s) overexpressed in LZ cells. Screening of 30,000 size-selected inserts yielded 5 positives, all hybridizing to probe pDR 1.6, but not to probe pDR7.8. These positive clones fell in two distinct classes with respect to their restriction map. When digested with restriction enzyme EcoRI, one group had two internal sites; the second group had no internal EcoRI site but had two internal BglII sites. Analysis of restriction enzyme sites in several overlapping clones and identification of poly A segments by preliminary DNA sequence analysis established the position of the 5' and 3' ends of these two groups of clones.

Subclones from the 5' region of each group were used to screen an additional 50,000 size-selected cDNA inserts; 12 positives were identified. These clones also fell into two groups. The two longest representative clones, lambda DR29 (4.1 Kb) and lambda DR11 (4.3 Kb) are represented schematically in FIG. 1. Individual clones belonging to these two groups were detected at that frequency in both rounds of screening of the cDNA library. This result suggests that mRNAs corresponding to each class of cDNA are transcribed at equivalent levels in drug susceptible cells. From the frequency of positive clones in our library, we estimate the abundance of RNAs homologous to pDR 1.6 to be approximately 0.05% to 0.1% of mRNAs larger than 2.3 Kb.

A. Analysis of lambda DR11

DNA sequence analysis of the larger (4.3 Kb) clone, lambda DR11, using three overlapping cDNA clones, suggested that lambda DR11 contained a complete coding sequence for a polypeptide. A polyA segment was identified at one end of this cDNA clone. At the opposite end, a DNA segment of 650 b.p. of continuous open reading frame was preceded by a 120 b.p. segment which included termination codons in all three reading frames. Within the first 250 b.p. of open reading frame, five AUG codons were identified.

Figure 2:
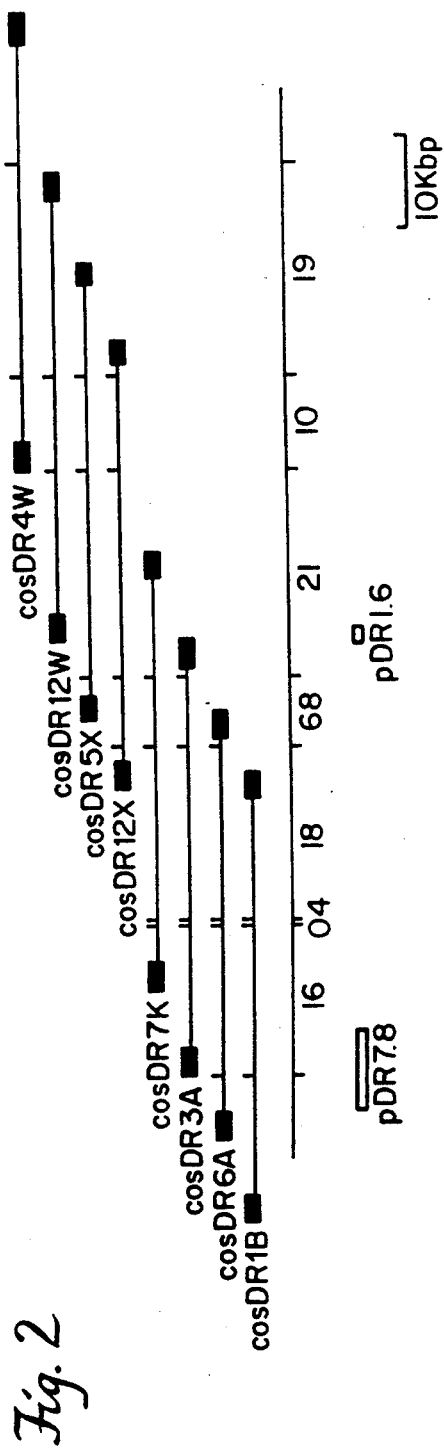
FIG. 2 is a composite map of eight cosmid clones overlapping the amplified domain cloned from multidrug resistant hamster LZ cells.

Analyses were carried out to determine the position of the gene encoding the mRNA homologous to lambda DR11 within the boundaries of the genomic domain cloned from LZ hamster cells. Eight cosmid clones carrying genomic DNA inserts overlapping the entire hamster cloned mdr domain were digested with BamHI and Southern blots probed with subcloned fragments of each family of cDNA clones. These are represented in FIG. 2. Each cosmid clone is presented as a DNA insert linked to the cosmid cloning arms (hatched boxes), with internal BamHI sites (small arrows). The corresponding BamHI map of the genomic domain (with size fragment in Kb) is presented along with the position of the two genomic subclones (pDR7.8 and pDR1.6) used to screen the cDNA library. Results of this analysis are presented in FIG. 3. The three subclones from the 5' end (pcDR 1.4), middle portion (pcDR 1.3) and 3' end (pcDR 1.5) portions of the cDNA insert of lambda DR11 show that the gene encoding this mdr mRNA is at least 75 Kb in size (FIG. 1). Genomic BamHI fragments of size 6.8, 18 (pcDR 1.4) 21 (pcDR 1.3), 10 and 19 Kb (pcDR 1.5) hybridized to this cDNA. A similar analysis with enzyme EcoRI also was consistent with a size of 75 Kb for the mdr gene. This value of the mdr gene size is in agreement with our previously reported estimate. Gros, P. et al.: *Proceedings of the National Academy of Sciences, U.S.A.*, 83:337-341 (1986).

This analysis also made it possible to deduce the direction of transcription within the cloned hamster mdr gene. Transcription proceeds from left (within the 18 Kb BamHI fragment) to right (within the 19 Kb BamHI fragment) within the domain shown in FIG. 2.

B. Analysis of lambda DR29

Similar hybridization studies and DNA sequence analysis of clone lambda DR29 indicated a weaker homology of this clone to the genomic domain cloned from LZ. As a result of these analyses, lambda DR11 was used for further expression studies.

II. Expression of mdr cDNA

The eukaryotic expression vector p91023B was used to determine whether the cDNA insert of lambda DR11 was capable of conferring multidrug resistance when expressed at significantly increased levels in drug sensitive cells. The basic features of this expression system have been described elsewhere. Kaufman, R. J. and Sharp, P. A., *Molecular and Cellular Biology*, 2: 1304-1319 (1982); Wong, G. G. et al., *Science*, 228: 810-814 (1985). Briefly, this vector has the pBR322 origin of replication and tetracycline resistance gene for propagation in *E.coli*. It also has eukaryotic regulatory elements that direct high levels of expression of the cloned cDNA: a) an SV40 origin of replication and enhancer element coupled to the adenovirus major late promoter (AdeMLP) and tripartite leader; b) a hybrid intron with a 5' and 3' splice site; c) the adenovirus VAI and VAII gene region; and d) the SV40 early polyadenylation signal. In addition, this vector contains a mouse dihydrofolate reductase (DHFR) cDNA which can be used as a dominant selectable maker in DHFR-sensitive cells. However, the selection protocols used did not rely upon expression of the intact DHFR cDNA.

Figure 4:
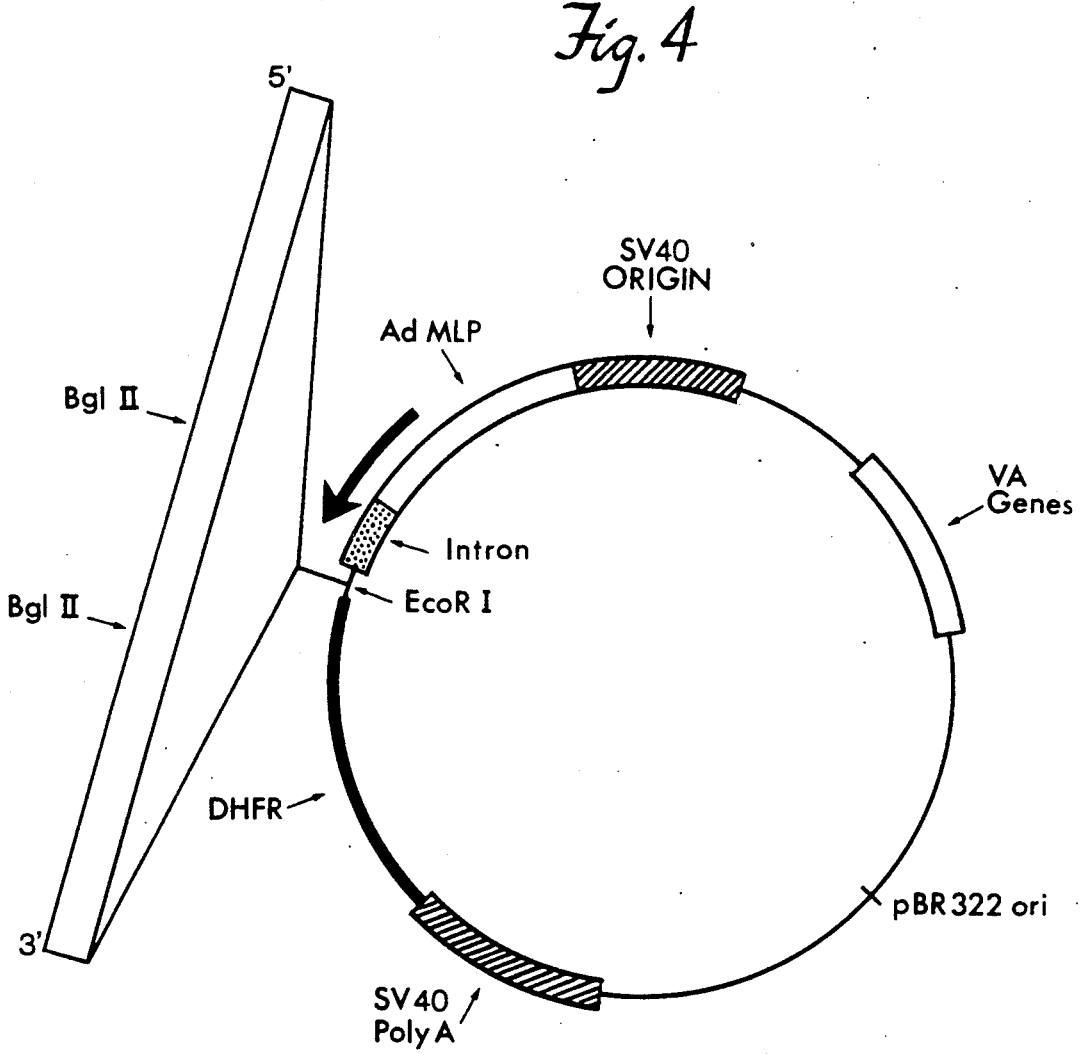
FIG. 4 is a schematic representation of the expression vector pDREX5.

The 4.3 Kb EcoRI insert of phage lambda DR11 was purified by agarose gel electrophoresis and cloned in the EcoRI site of plasmid p91023. Tetracycline resistant transformants of *E. coli* strain DH1 carrying recombinant p91023 plasmid containing the cDNA insert of phage lambda DR11 in the two possible orientations were identified, amplified and the plasmid DNA purified. Two constructs were isolated: pDREX4 had the 5' end of the inserted cDNA immediately downstream the 3' splice site of the hybrid intron (sense orientation) while pDREX5 had the cDNA in the opposite orientation (antisense orientation) and was used as a control for transfection experiments. Gros, P. et al., *Nature*, 323: 728-731 (1986), the teachings of which are incorporated herein by reference. A schematic diagram of pDREX4 is presented in FIG. 4. The large arrow indicates the direction of transcription.

A. Assessment of resistance to Adriamycin

Figure 5I:
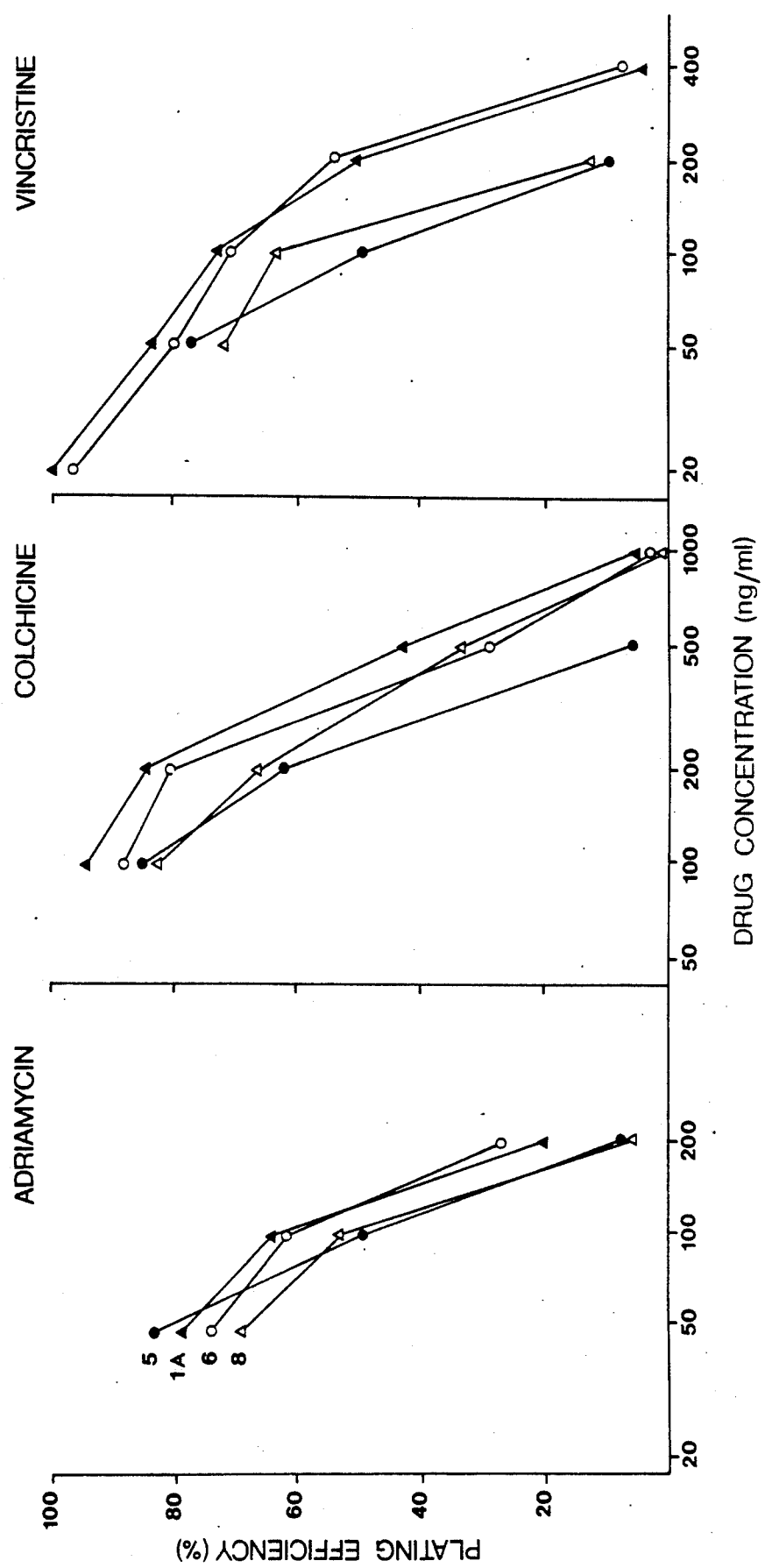
FIG. 5i is a graphic representation of the relative plating efficiency of four Adriamycin resistant clones transfected with pDREX4 and tested for crossresistance to other cytotoxic drugs.

The drug sensitive CHO subline LR73 can be transfected at high efficiency with plasmid DNA and was selected for expression studies. Pollard, J. W. and Stanners, C. P., *Journal of Cellular Physiology*, 98 571-586 (1979). In an initial experiment, LR73 cells were transfected with plasmids pDREX4 and pDREX5 (FIG. 5a-5h) and subcultured in medium containing the chemotherapeutic agent Adriamycin (ADM) at 0.05 mcg/ml (5a, 5b) and 0.1 mcg/ml (see Example 3). Previous results from chromosome mediated gene transfer experiments had shown that transfer of multiple copies of mdr gene was necessary for recipients cells to survive a single step selection in Adriamycin (0.1 mcg/ml) and that the frequency of spontaneous drug resistant colonies in control mouse and hamster cells plated at that concentration of Adriamycin was extremely low (less than 1 in $5 \times 10^7$ cells). This concentration of Adriamycin (0.1 mcg/ml) was therefor used to assess the ability of the cDNA to confer a true Adriamycin resistance phenotype. The lower concentration of Adriamycin (0.05 mcg/ml) was chosen to quantitate a possible increase in colony numbers above background levels (2 to 4 per $10^6$ cells) generated by the introduction of pDREX4 and pDREX5 in LR73 cells. Transfection of pDREX4 into LR73 cells resulted in a 200 fold increase in the number of colonies resistant to 0.05 mcg/ml Adriamycin (FIG. 5, a vs b) over background colony numbers observed in dishes from control LR73 cells transfected with pDREX5 (FIG. 3a, 3b), p91023B or salmon sperm (SS) DNA. At the higher dose of Adriamycin (0.1 mcg/ml), pDREX4 behaved as a dominant selectable marker. That is, although no colonies were observed in control groups transfected with pDREX5 (FIG. 5, c), p91023 or SS DNA, an average of 75 to 150 colonies emerged on dishes of LR73 cells transfected with pDREX4 (transfection efficiency of 200 CFU/$10^6$ cells/mcg DNA).

B. Assessment of resistance to colchicine

To determine whether the resistance phenotype conferred upon transfection by plasmid pDREX4 was limited to Adriamycin or extended to other drugs, a second experiment was conducted in which selection was carried out in medium containing a different cytotoxic drug, colchicine. LR73 cells were transfected with the same panel of DNAs and subcultured in medium containing colchicine at 0.1 mcg/ml or 0.3 mcg/ml. These two drug concentrations have been shown to correspond to a selection stringency similar to the Adriamycin selection (0.05 and 0.1 mcg/ml), used previously. Results from this second experiment showed that pDREX4 conferred colchicine resistance to LR73 cells in a pattern very similar to the one observed when Adriamycin was used as a selective agent. At the low colchicine concentration (0.1 mcg/ml), a 100 to 200 fold increase in colony number was observed in cells transfected with pDREX4 versus the control groups (FIG. 5, e vs f). At the high drug concentration (0.3 mcg/ml), pDREX4 behaved as a dominant selectable marker (FIG. 5, g vs h), although very few colonies were detected at this level of selection.

C. Assessment of cross resistance to drugs

To further assess the role of the mdr cDNA in the pleiotropic drug resistance phenomenon, four individual clones originally selected in Adriamycin at 0.1 mcg/ml were examined for their level of cross resistance to Adriamycin (ADM), colchicine (COL) and vincristine (VCR) (FIG. 5i) Cells from clones 5, 1A, 6, 8 and the control LR73 line were seeded in medium containing increasing concentrations of the drugs and the plating efficiency was measured at day 14. Results from this experiment show that the 4 clones tested were cross resistant to ADM, COL and VCR and that their resistance phenotype was qualitatively and quantitatively very similar. A 10- to 20-fold increase in resistance against the three drugs tested was observed in the four clones, compared with the LR73 control. For the four clones, D10 (defined as the dose necessary to produce a 10% plating efficiency) was greater than 200 ng/ml for ADM, VCR and greater than 500 ng/ml for COL. For the LR73 control, D10 was less than 20 ng/ml for ADM, VCR and less than 50 ng/ml for COL. Clones 1A and 6 were slightly more drug resistant than clones 5 and 8; this difference was particularly evident in the response of the 4 clones to VCR.

These results indicate that pDREX4 can confer, upon transfection into drug sensitive cells, the full multidrug resistance phenotype observed in multidrug resistant lines selected in vitro.

The three drugs used in the work described (adriamycin, colchicine and vincristine) are members of two important classes of drugs (the anthracyclines and the alkaloids) which include a number of commonly used therapeutic compounds. The anthracyclines also include daunorubicin, a widely used antibiotic, and alkaloids include vinblastine, vinleurosine and vinrosidine. Cross resistance to drugs in these two classes is known to occur. Kartner, N. et al., *Science*, 221:1285-1288 (1983) In light of the fact that it has been shown that all other multidrug resistant cell lines resistant to anthracyclines and alkaloids are also resistant to actinomycin D (a widely used antibiotic), it is reasonable to expect that the multidrug resistant cells described herein will also be resistant to actinomycin D. Biedler, J. and H. Riehm, *Cancer Research*, 30:1174-1184 (1970); Johnson, R.K. et al., *Cancer Treatment Reports*, 62:1535-1547 (1978).

III. Genomic DNA analysis of transfected cells

Genomic DNA from individual transfected clones was analyzed by Southern blotting to determine the copy number and arrangement of the transfected plasmid in drug resistant colonies and to determine whether amplification of the endogenous copy of the hamster gene contributes to the resistant phenotype of the transfectants. Southern, E. M., *Journal of Molecular Biology*, 98: 503-517 (1975).

Figure 6A:
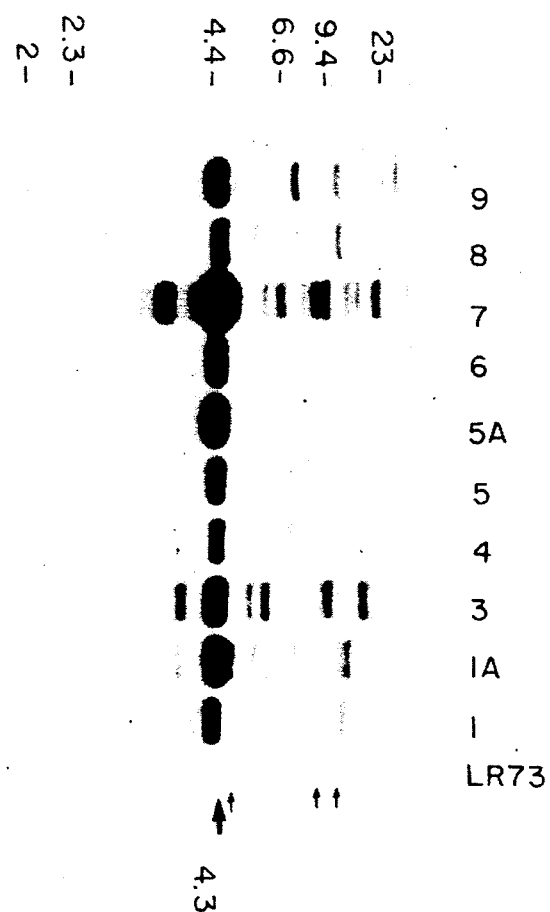
FIGS. 6a and b are Southern blots of genomic DNA from clones transfected with pDREX4.
Figure 6B:
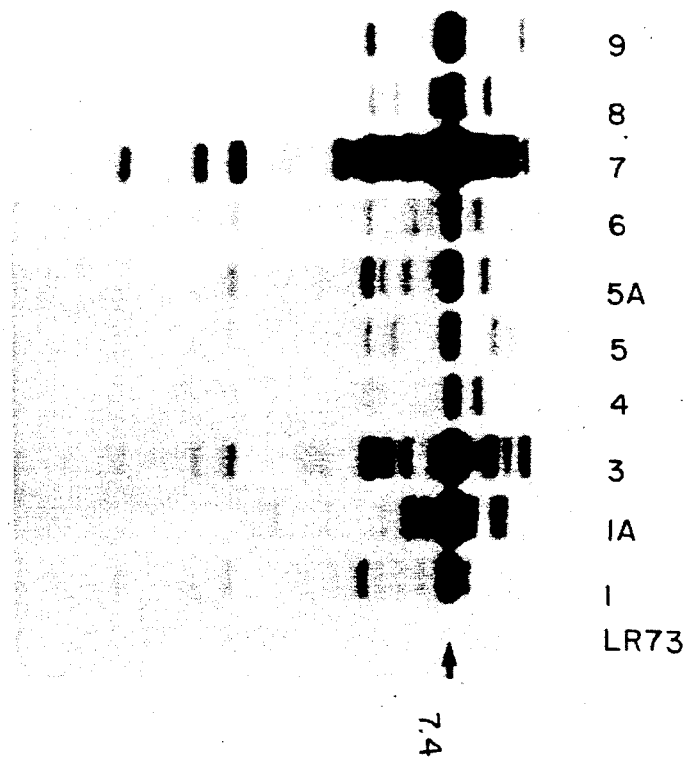

Genomic DNA from 10 individual clones was digested to completion with EcoRI, an enzyme that liberates the 4.3 Kb EcoRI cDNA fragment from the construct pDREX4. Duplicate blots were hybridized to either the cDNA insert (FIG. 6a) or the plasmid probes (FIG. 6b). When the 4.3 Kb EcoRI cDNA fragment was used as hybridization probe, it also detected three EcoRI fragments present at single copy level in LR73 cells and in each transfected clone (FIG. 6a); these represent the endogenous copy of the hamster mdr gene. This result demonstrates that amplification of the hamster gene is not responsible for the multidrug resistance phenotype of LR73 transfectants. This 4.3 Kb cDNA fragment detects an intensely hybridizing 4.3 Kb band representing the intact cDNA EcoRI fragment; copy number in individual clones varied between 10 (clone 5) and 50 to 60 copies (clone 7). Clone 1A, which showed a higher level of resistance (FIG. 6b) than clone 5, has a higher copy number of the transfected cDNA than clone 5. In addition to this 4.3 Kb band, the 4.3 Kb cDNA probe detects a large number of EcoRI fragments whose size is larger than 4.3 Kb and whose copy number varies greatly among clones, but which seems to correlate with the copy number of the 4.3 Kb fragment. This suggests that these new fragments most likely originate from integrated copies of pDREX4, the integration of which has resulted in breakage of the 4.3 Kb cDNA fragment. When the cloning vector p91023B was used as hybridization probe on this blot, a similar pattern emerged. Multiple copies of the expected 7.4 Kb fragment (FIG. 6b) were detected in each of the transfectants and copy numbers were similar to those of the 4.3 Kb fragment detected by the cDNA probe (FIG. 6a). Numerous additional bands of various sizes are also detected by the plasmid probe. It is difficult to determine when, during the process of DNA uptake and clonal expansion of resistant colonies, rearrangements of pDREX4 occurred.

These results clearly demonstrate that the multidrug resistance phenotype of the clones tested is linked to the presence of multiple copies of pDREX4. They also make it clear that survival in the test concentration of Adriamycin requires the expression of multiple copies of pDREX4.

IV. mRNA measurement in transfected cells

A qualitative and quantitative analysis of transcription of the transfected mdr cDNA was performed. cDNA molecules introduced in the EcoRI site of p91023B were transcribed into a hybrid mRNA containing the cDNA sequence flanked by the adenovirus tripartite leader at the 5' side and by the mouse DHFR sequence serving as a non translated sequence at the 3' side. Wong, G. G. et al, *Science*, 228: 810–814 (1985) As a result, it is possible to distinguish between the endogenous mdr mRNA transcribed from the hamster gene and the mRNA transcribed from the transfected cDNA construct (about 1.1 Kb larger). Total cellular RNA was extracted from eight individual clones and analyzed by Northern blotting (FIG. 7a). Alwine, J. et al., *Proceedings of the National Academy of Sciences, U S.A.*, 74: 5350–5354 (1977). When a cDNA subclone (pcDR 1.3) was used as a hyrbidization probe, it detected in all the transfectants a hybridizing band approximately 6 Kb in size, as estimated by comparison with the 28 and 18S ribosomal bands. The shorter endogenous mdr cellular transcript (about 5 Kb) is not detected on this autoradiograph (2 hrs exposure, FIG. 7a) and can be visualized only after a much longer exposure of the blot (48 hrs exposure, FIG. 7b). Hybridization of the blot to a mouse DHFR probe supports the idea that the 6 Kb band is a hybrid mRNA containing both the mdr cDNA and the DHFR sequences. Another feature of this Northern blot (FIG. 7a) is the intense lane-specific background obtained with the cDNA probe, most obvious after longer exposure of the blot. It seems likely that this background represents hybridization of the probe to truncated mRNA species. Such mRNA species could be transcribed from rearranged copies of the transfected cDNA detected in the genomic DNA analysis. Increased levels of mdr were shown to be present in all drug resistant transfectants tested (FIG. 7a). A dot blot analysis was performed to more accurately quantitate the level of expression of the transfected mdr cDNA in these clones (FIG. 7c). Results showed that all transfectants present a minimum of an 8-to-16-fold increase in mdr cDNA expression when compared with the background level of mdr RNA of LR73 (not detectable at this exposure time).

The results of this work show that the multidrug resistance phenotype can be conferred by increased expression of this unique cDNA obtained from drug sensitive cells. Drug resistance in these clones requires a high level of transcription of the transfected cDNA expressed as a 6 Kb hybrid mRNA. As indicated, there is apparently a small group of related mdr genes, one of which is described above. Elucidation of the role and function of other members of the mdr group awaits further characterization of cDNA clones. It is possible that amplification/overexpression of more than one mdr gene is necessary to achieve the very high levels of resistance detected in LZ and C5 cells. That is, the loss of proportionality, observed at very high levels of resistance (up to 1000 fold), between mdr expression levels (or gene copy number) and relative drug resistance may occur because of a synergistic effect of amplification or overexpression of more than one such mdr gene. It should be possible, using the methods described above, to identify and characterize additional members of the mdr gene family and assess their interaction in conferring a multidrug resistance phenotype upon mammalian cells.

V. Nucleotide sequence of lambda DR11 mdr gene and deduced amino acid sequence of encoded protein The nucleotide sequence of the mdr gene of lambdo DR11 is shown in FIG. 8A, 8B, and 8C. The amino acid sequence, deduced from the DNA sequence of the mdr gene is presented in FIG. 9. The nature and function of the mature gene product encoded by the cloned cDNA described above is unclear. Analysis of the nucleotide sequence of the cDNA suggests that the encoded protein or glycoprotein is a large molecule which has potential glycosylation sites, and is most likely to be a membrane protein. The encoded protein appears to contain (starting at the 5' end) three hydrophobic domains, a neutral domain, three additional hydrophobic domains and a second neutral domain. The membrane-transversing portions of the protein most likely occur within the hydrophobic domains. In addition, the encoded protein binds ATP and has ATP binding sites within its neutral domains. These observations are compatible with the hypothesis that increased synthesis of this membrane protein may alter membrane physiology to cause decreased intracellular drug accumulation.

VI Applications of the multidrug resistance phenotype conferred by the mdr gene

It is possible to make use of the discovery that a multidrug resistance phenotype can be conferred by introduction and increased expression of mdr DNA into drug-sensitive mammalian cells in at least five contexts:
A. as a dominant selectable marker;
B. as an amplifiable marker;
C. as a diagnostic tool;
D. in the design of new drugs; and
E. in gene therapy.

A. Dominant selectable marker

When properly expressed, the cDNA clone described, and other mdr gene family members, allows the production of a dominant selectable trait. That is, when an mdr gene such as the 4.3 Kb cDNA contained in plasmid pDREX4 (described above) is introduced into drug-sensitive cells under conditions appropriate for its expression at increased levels, the drug sensitive cells become drug resistant and are able to survive and form colonies even in media containing drug levels which normally cause death of drug-sensitive cells.

For example, it is possible to introduce the 4.3 Kb EcoRI fragment of lambda DR11 into an expression vector (such as p91023 described above) along with one or more genes of interest. Transfection of drug sensitive cells with the resulting plasmid DNA will result in uptake by some of the cells of the 4.3 EcoRI fragment and the associated additional gene(s); these cells will thus become multidrug resistant. Other cells will fail to take up the 4.3 EcoRI fragment/additional gene(s) hybrid and remain drug sensitive. Subsequent culturing of the cell mixture in drug-containing media will result in the survival of only those cells into which the 4.3 EcoRI DNA fragment and additional gene(s) have been incorporated.

Introduction of an mdr gene not only confers drug resistance, but also confers resistance to a number of drugs, which are unrelated structurally and functionally. Conventional selectable markers convey resistance to only one drug and thus do not provide for a control which can be used to determine the effect, if any, of the selecting drug on surviving cells. It is possible to use a wide variety of drugs in transfection experiments as a selection means. A cDNA clone which confers multi-drug resistance can also be used as a vehicle for moving hybrid genes into new host cells and monitoring their presence. That is, it would be possible to engineer a DNA sequence which includes the mdr gene and one (or more) genes of interest; incorporate the hybrid sequence into a plasmid; transfect an appropriate host cell with the plasmid and monitor their presence in cells by culturing in media containing more than one drug. Cells which contain the mdr gene and the gene(s) of interest will survive and those which do not will die.

2. Amplifiable marker

The cDNA clone can be used as an amplifiable marker; by increasing stepwise the concentration of a drug or drugs used in selecting for cells containing the cDNA clone, it is possible to obtain a higher copy number (increased level of gene expression). As a result, it is also possible to induce a high copy number of a second gene carried by the marker and thus, artificially and selectively induce increased expression of the second DNA sequence.

C. Diagnostic tool

Because the gene cloned in pcDR27 (the mouse cDNA clone containing the 4.3 Kb DNA fragment described above) is highly conserved at the nucleotide level in mouse, hamster and human cells, the clone can be used to monitor chemotherapeutically treated human tumors for alterations in the structure of the gene or in its level of expression. Similarly, other members of the mdr gene family can be used for monitoring such tumors and detecting the presence of alterations in the corresponding gene's structure or expression level.

A variety of techniques can be used in monitoring tumor cells for the mdr gene. For example, modifications or alterations in the structure of the mdr gene(s) can be detected through use of Southern blotting analysis. In this technique, DNA from the tumor cells to be analyzed is extracted from sample cells and cut or digested with a restriction enzyme. The resulting DNA fragments are separated on the basis of size (e.g., by gel electrophoresis) and bound to a nitrocellulose filter. The clone (pcDR27) containing the 4.3 Kb cDNA fragment is labelled (e.g., radiolabelled) and used to probe the nitrocellulose-bound tumor cell fragments for fragment(s) containing complementary sequences. That is, under appropriate conditions, the cDNA fragment will "recognize" complementary fragments and hybridize to them. Autoradiography of the nitrocellulose filter containing the bound fragments demonstrates the occurrence of radiolabelled probetumor cell DNA complexes. This method makes it possible to determine the occurrence of modifications in mdr genes in sample tissues and the number of genes having such modifications. Other methods of detecting modifications of the mdr gene(s) in tumor cells include, for example, Northern blotting, useful for detecting the presence of mRNA of interest, in situ hybridization, which can be used for detecting either DNA or RNA (and thus the level of expression (i.e., the level of expressed RNA) of the mdr gene(s)).

Antibodies, either polyclonal or monoclonal, raised against conserved portions of the protein(s) encoded by the mdr gene(s) can also be used in a diagnostic context. Because these highly conserved portions of the encoded protein(s) are also highly specific to the mdr gene product(s), an assay using such serological reagents is highly specific. Antibodies specific to these regions can be used, for example, in immunofluorescence assays.

Using cloning techniques, significant amounts of the protein(s) encoded for by the highly conserved regions of an mdr gene can be produced and isolated. These protein segments or polypeptides can be used to produce antibodies by standard antibody production techniques. For example, if polyclonal antibodies are to be produced, the protein segments can be used to immunize a host (e.g., a rabbit or a rat) and antibodies to the protein obtained from serum from that host. If monoclonal antibodies are to be produced, it would be possible to use cells which produce antibodies to the protein encoded by the mdr gene regions in typical fusion techniques used to form hybridoma cells. These techniques are well known and involve fusing an antibody-producing cell with a cell having immortality (e.g., a myeloma cell) to produce a fused cell hybrid which is immortal and capable of producing the desired antibody (in this case, antibody to conserved portions of the protein(s) encoded by the mdr gene(s)). The hybrid cells are then cultured under conditions appropriate for producing antibody; antibody is subsequently collected from the cell medium. Techniques for producing monoclonal antibodies are well known. See, for example, U.S. Pat. No. 4,172,124 and U.S. Pat. No. 4,196,265, Koprowski et al., the teachings of which are hereby incorporated by reference.

D. Design of new drugs

The above information makes it possible to design new drugs or modify presently available drugs to increase their activity toward (i.e., ability to have the desired effect on) drug-resistant cells. For example, purification of large quantities of the mature protein encoded by the specific mdr mRNA will allow study of the three dimensional structure of the protein. This investigation will be aided by the availability of multiple antibodies directed toward segments of the polypeptide chain. Such antibodies will allow study of the molecular arrangement of the protein(s) encoded by the mdr gene(s) in cell membranes.

As a result of this combined assessment, it will be possible to determine the nature of the cellular modifications produced by increased amounts of the encoded protein(s) and to define the specific mechanism by which the protein imparts multidrug resistance. Knowledge of the spatial arrangement of the protein will make it possible to design new drugs (or modify the structure of those now being used) which will be affected by the action of the protein(s) and thus better able to enter cells.

E. Gene therapy

An important limitation to the use of chemotherapeutic drugs in treating patients is the extensive depletion of bone marrow which occurs. As a result, the patient is unable to fight off a variety of bacterial, fungal and viral pathogens. The cDNA of the present invention, or another member of the mdr gene family, can be used to alleviate this problem. This could be accomplished by inserting the cDNA described, or other mdr gene, into an appropriate amphotropic or ecotropic retroviral construct, which can then be used to infect normal bone marrow cells. This approach can be valuable, for example, in the situation in which bone marrow is removed from a patient, the gene is inserted into the marrow and the resulting engineered marrow reintroduced into the patient. This can be used in anticipation of chemotherapy or after the effects of such treatment on bone marrow have become evident. This approach can also be valuable in bone marrow transplants, in which the patient's initial bone marrow is replaced by marrow into which the mdr gene has been incorporated. In either case, the bone marrow cells containing the mdr gene will consequently express high levels of the specific mdr mRNA. As a result, they will be resistant to the effects of the chemotherapeutic drugs and able to repopulate the depleted marrow. It will be possible to administer higher concentrations of the chemotherapeutic drug(s) to the individual without destroying the transplanted bone marrow. This should contribute to the ability of the patient to survive.

This invention is further illustrated by the following examples, which are not to be seen as limiting in any way.

EXAMPLE 1

Construction and screening of cDNA library

Total cellular RNA from the BALB/c mouse cell line 70Z/3 was prepared using guanidinium hydrochloride; the polyA fraction of the RNA was purified by chromatography on oligodT cellulose. Ten micrograms of polyA+ RNA was used for reverse transcripgrams tase directed first stand DNA synthesis. The reaction was carried out for 10' at 20° C. and then 45' at 42° C. in the presence of 14 mM mercaptoethanol, 1.5 mM MeHgOH, oligo d(pT) 12-8 (100 mcg/ml, Collaborative Research), 55 mM Tris Cl pH 8.3 (42° C.) 10 mM $MgCl_2$, 5 mM Na pyrophosphate, 0.38 mM each dNTP, 10 mM DTT, 10 mM KCl, and 150 units of mouse leukemia virus (MoLV) reverse transcriptase (BRL). The second strand was synthesized with E. coli DNA polymerase I (300 units/ml) in the presence of ribonuclease H (125 units/ml) for 16 hours at 12° C. in 20 mM Tris Cl (pH 7.5), 2 mM $MgCl_2$, 10m, $(NH_4)_2SO_4$, 100 mN KCl, BSA (50 mcg/ml), 10 mM DTT and 0.04 mM each dNTP. The first strand and second strand synthesis reactions were stopped by phenol/chloroform extractions and the nucleic acids were recovered by ethanol precipitation. The EcoRI sites were methylated after addition of S-adenosylmethionine to 50 uM and 40 units EcoRI methylase, by incubation at 37° C. for 30 minutes. Kinased EcoRI linkers (Collaborative Research, 300 ng) were then added to the double stranded cDNA by overnight ligation at 16° C. in a final volume of 30 ul with T4 DNA ligase. The reaction was then diluted to 100 ul in EcoRI digestion buffer and the DNA was digested with 200 units of EcoRI (NE-Biolabs) for 2 hours at 37° C. The reaction was stopped by addition of EDTA to 25 mM and the nucleic acids were precipitated with ethanol. The cDNA was dissolved in 10 ul of TE (10 mM Tris, pH 8.0, 1 mM EDTA) and electrophoresed on a 1% agarose gel (Tris borate buffer, pH 8.0).

The portion of the gel corresponding to DNA of size greater than 2.3 Kb was cut out and the DNA was recovered by electroelution, phenol/chloroform extraction and ethanol precipitation. Portions of 50 ng of cDNA were ligated to 8 ug of EcoRI digested lambda gtll cloning arms by T4 DNA ligase overnight at 14° C. The ligation mixture was then packaged into phage particles in vitro (Promega Biotech) and the library was plated onto E. coli Y1088.

The plated library was screened with pDR 1.6 and pDR 7.8 by plaque hybridization. Primary plugs containing positive clones (4 mm diameter, about 100 clones) were collected, plate lysates were prepared, and rapid isolation of phage DNA was performed. Phage DNA were digested with EcoRI, and other enzymes, electrophoresed on 1% agarose gel, and blotted to a hybridization membrane. The blots were probed with the screening probe. A preliminary restriction map of the clones could be obtained by this approach and only clones with the largest size inserts were further purified.

The two longest lambda phage cDNA inserts representative of the two independent populations of clones isolated from the mouse cDNA library are represented schematically in FIG. 1. The group exemplified by clone lambda DR29 contains 2 internal EcoRI sites, as evidenced by the fact that digestion of several clones yielded constant 1.1 Kb and 0.9 Kb fragments and a third fragment of variable size. The second group, represented by clone lambda DR11, did not show internal EcoRI sites. Restriction analysis with enzymes BglII and EcoRI in combination yielded fragments of size 1.5 Kb and 1.3 Kb with a third fragment of variable size. The 1.5 Kb and 1.4 Kb BglII/EcoRI fragments as well as the 1.3 Kb internal BglII fragment of cDNA insert from phage lambda DR11 were subcloned in puc19 digested with EcoRI/BamHI or BamHI respectively to generate subclones pcDR 1.5, pcDR 1.4 and pcDR 1.3.

EXAMPLE 2

Figure 3C:
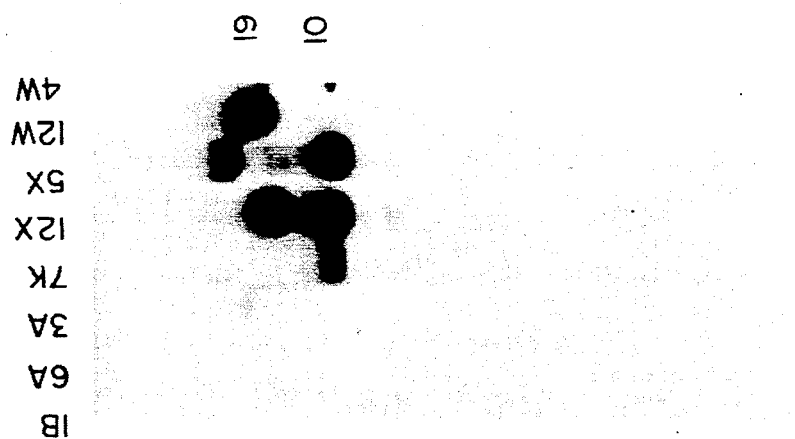
FIGS. 3a b, and c are blots showing the results of hybridization analyses of cDNA subclones of lambda DR11 to eight cosmid DNA clones.
Figure 3B:
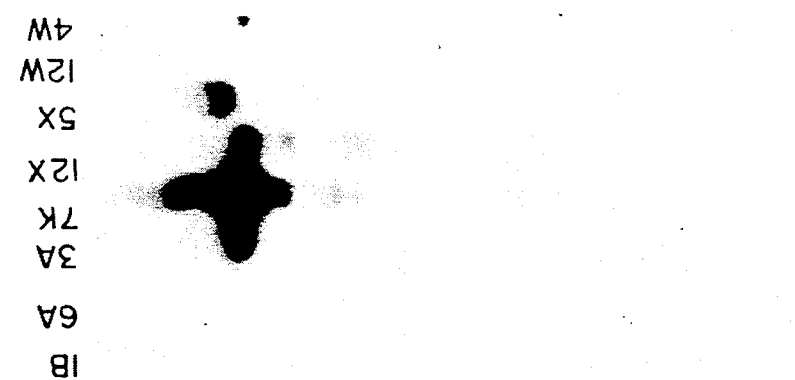
Figure 3A:
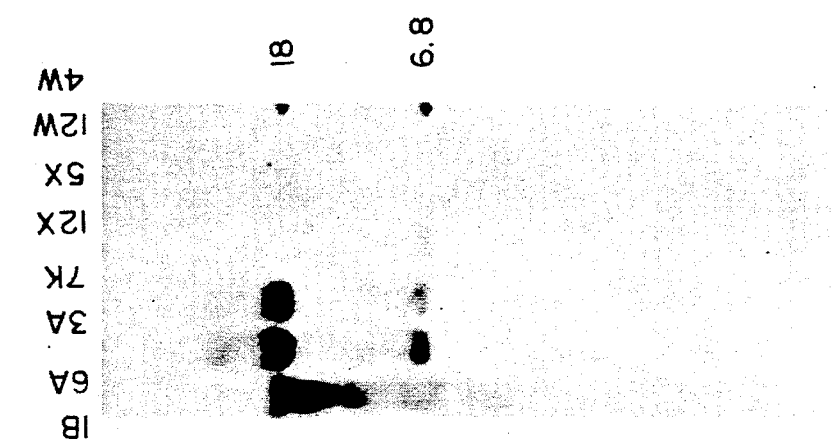

Mapping of the cloned cDNA to the amplified unit cloned in the cosmid vectors from multidrug resistant LZ hamster cells Two micrograms of cosmid DNA from clones cosDR1B, 6A, 3A, 7K, 12X, 5X, 12W and 4W were digested with BamHI. Digestion products were separated by electrophoresis of a 1% gel containing 0.04 M Tris acetate pH 8, 2 mM EDTA, and transferred to a hybridization membrane (Zetabind, Biorad) and the blots were hybridized to $P^{32}$ labeled DNA inserts from cloned pcDR 1.4 (FIG. 3a), pcDR 1.3 (FIG. 3b) and pcDR 1.5 (FIG. 3c). Hybridization was carried out for 6 hours at 42° C. in the presence of 5 x SSC, 5x Denhardt's solution, 50% formamide, 50 mcg/ml denatured salmon sperm DNA and $1 \times 10^6$ cpm of each of the hybridization probes synthesized by the Klenow fragment of *E. coli* DNA polymerase I using random oligodeoxynucleotide primers. Blots were washed at a final stringency of 0.1 x SSC, 0.1% SDS at 65° C. and exposed to X-ray film for four hours with an intensifying screen. The arrows in FIG. 3 indicate the position and size in Kb of hybridizing internal BamHI fragments from individual overlapping cosmid clones. Other hybridizing fragments represent hybrid fragments containing cosmid vector pSAE (approximately 9 Kb).

EXAMPLE 3

Transfection of cDNA clones into drug sensitive hamster cells

DNA transfection of LR73 hamster cells was performed according to a modification of standard protocols: $5 \times 10^5$ cells were plated in 100 mm dishes. Sixteen hours later they were exposed for 20 minutes at 20° C. to 10 mcg of a calcium phosphate precipitate of plasmid pDREX5 (FIG. 5a, c, e, g, i) or plasmid pDREX4 (FIG. 5a, b, d, f, h, i) in a final volume of 0.5 ml. Fresh medium was added and the cells were further incubated at 37° C. for 6 hours. The cells were then chocked with glycerol (15%, 3 minutes at 37° C.) and, 48 hours later, plated in four selective media: Adriamycin at 0.05 mcg/ml (FIG. 5A, a,b) or 0.1 mcg/ml (FIG. 5a, b, i) and colchicine at 0.1 mcg/ml (FIG. 5e, f, i) or 0.3 mcg/ml (FIG. 5g, h, i). Five weeks later, the colonies were fixed 4 hours with 4% formaldehyde and stained with 0.1% methylene blue. Also, 12 individual clones were isolated and further expanded in culture. The drug resistance phenotype of individual transfectants was characterized. Four individual Adriamycin resistant clones transfected with pcDREX4 and selected in 0.1 mcg/ml Adriamycin were tested for cross resistance to other cytotoxic drugs. Five hundred cells of clone 6, 1A, 5, 8 and control LR73 cells were plated in 35 mm dishes containing 3 ml of medium supplemented with increasing concentrations of drugs Adriamycine ( 0, 0.05, 0.1, 0.2, 0.5 and 1 mcg/ml), colchicine (0, 0.1, 0.2, 0.5, 1, 2 mcg/ml) and vincristine (0, 0.02, 0.04, 0.1, 0.2 and 0.4 mcg/ml). Cultures were fed with fresh drug containing medium at day 5 and day 10. They were fixed with formaldehyde at day 14, stained with methylene blue and colonies ( 30 cells/colony) were counted. Results are presented in FIG. 5b as the relative plating efficiency of each clone expressed as a percentage of the plating efficiency of individual control cells grown in the absence of drugs versus the logarithm of the drug concentration.

EXAMPLE 4

Southern analysis of genomic DNA of cells transfected with pDREX4

Individual colonies first selected in Adriamycin at 0.1 mcg/ml were expanded in culture and genomic DNA was isolated from these colonies after proteinase K digestion and serial phenol/chloroform extractions. Milbrandt, J.D. et al., *Molecules and Cellular Biology*, 3:1266–1273 (1983). Ten micrograms of genomic DNA from clones 1, 1A, 3, 4, 5, 5A, 6, 7, 8 and from the hamster LR73 line were digested with a 5-fold excess of restriction enzyme EcoRI. The reaction mixture was phenol extracted and the nucleic acids were recovered by ethanol precipitation. Appropriate controls to assure complete digestion and equal loading of DNA on the gels were included. Digestion products were electrophoresed in a 1% agarose gel containing 0.04 M Tris acetate (pH 8), 0.002 m EDTA. The gel was transferred to a hybridization membrane (Zetaprobe, Biorad) and the blot was hybridized to $10^7$ cpm of $P^{32}$ labeled insert DNA from pcDR 1.3 (FIG. 6, panel a) or to the expression vector p91023 (FIG. 6, panel b) in the presence of 50% formamide, 5x Denhardt's solution 5x SSPE, 10 mcg/ml denatured salmon sperm DNA for 48 hours at 42° C. The blots were washed to a final stringency of 0.1 x SSC, 0.1% SDS at 65° C. for 1 hour. The blots were exposed to X-ray films for 36 hours at −80° C. with an intensifying screen. Small arrows in panel a of FIG. 6 indicate the position of the hybridizing fragments corresponding to the endogenous copy of the hamster gene homologous to the probe. The large arrow on that panel indicates the position of the intact 4.3 Kb cDNA insert released after EcoRI digestion of pDREX4. The large arrow on panel b of FIG. 6 shows the position of the intact 7.4 Kb p91023 fragment released by EcoRI digestion of the transfected pDREX4 construct. Size markers are the HindIII digestion product of phage lambda.

EXAMPLE 5

Transcription analysis of cells transfected with pDREX4

Total cellular RNA was extracted with guanidinium hydrochloride from Adriamycin-resistant clones 1A, 1, 3, 5, 6, 8, 9, 10 and from the control hamster line LR73. The results of assays are shown in FIG. 7, panels a-c. Ten micrograms of RNA was electrophoresed in a 1% agarose gel (a) containing 7% formaldehyde, 0.02 M MOPS (pH 7.0) 0.05 M sodium acetate, and 0.001 M EDTA. The RNA was transferred from the gel onto a reusable hybridization membrane (Gene Screen Plus, Dupont) by electroblotting in a buffer containing $0.0 \pm 6$ M Tris acetate, 0.001 M EDTA at 4° C. for 3 hours. The blot was probed with $5 \times 10^6$ cpm of $P^{32}$-labeled cDNA subclone pcDR 1.3 (10 ng) at 62° C. for 1 hour. The blot was exposed to X-ray films at −80° C. with an intensifying screen for 2 hours (a). To detect the background level of mRNA in LR73 control hamster cells, the blot was exposed for 48 hours (b). The large arrow on panel a indicates the position of the major 6 Kb transcript homologous to pcDR 1.3. A dot blot analysis was carried out to quantitate the level of specific mRNA expressed in the transfected clones (c). Five micrograms of total cellular RNA were denatured in a solution containing 7% formaldehyde and $7 \times SSPE$ at 65° C. for 10 minutes. RNA samples were serially diluted and loaded onto a nitrocellulose membrane, using a 90 wells manifold (Hybridot, BRL). The blot was hybridized to $1 \times 10^6$ cpm of $P^{32}$ labeled pcDR 1.3 in $5 \times SSPE$, 0.5% SDS, 5x Denhardt's solution, 50 mcg of denatured salmon sperm DNA per ml, for 6 hours at 60° C. Washing conditions were $0.1 \times SSC$, 0.1% SDS, 60° C. for 1 hour. The blot was exposed to X-ray films for 24 hours at −80° C. with an intensifying screen. The RNA dilution factor (1 to 128) indicated that the cDNA is expressed at levels 32-to 64-fold higher than the background LR73 level.

We claim:

1. An isolate DNA sequence as forth in FIG. 8A, 8B and 8C or a nucleotide sequence which hybridizes to said sequence under stringent conditions and which confers a multidrug resistance phenotype on a drug-sensitive mammalian cell when introduced and expressed in said cell.

2. A eukaryotic expression vector containing a dominant selectable marker capable of expression in a mammalian cell comprising:
   a) the 4.3 Kb EcoRI DNA fragment of lambda DR11 or a DNA fragment which hybridizes thereto under stringent conditions and which is capable of conferring the multidrug resistance phenotype when transfected into drug sensitive cells;
   b) a pBR322 origin of replication; and
   c) a promoter sequence.

3. The vector of claim 2 which is pDREX4.

4. A method of conferring a multidrug resistance phenotype on a drug sensitive mammalian cell, comprising the steps of:
   a) introducing into said cell a 4.3 Kb EcoRI DNA fragment of lambda DR11 as set forth in FIGS. 8A, 8B, and 8C, or a nucleotide sequence which hybridizes to said sequence under stringent conditions and "after sequence", which confers a multidrug resistance phenotype on a drug-sensitive mammalian cell when introduced and expressed into said cell,
   b) maintaining said cells under conditions conducive to transcription of said DNA;
   c) selecting those cells that exhibit the multidrug resistance phenotype.

5. A method of increasing expression of a heterologous gene within a cell, comprising the steps of:
   a) constructing an expression vector comprising a heterologous gene and a multidrug resistance gene having the sequence set forth in FIG. 8A, 8B and 8C, or a DNA sequence which hybridizes to said sequence under stringent conditions and which confers a multidrug resistance phenotype on a drug-sensitive mammalian cell when introduced and expressed in said cell.
   b) transfecting an appropriate host cell with said vector;
   c) selecting host cells which contain said vector by culturing said cells in drug-containing media; and
   d) culturing cells selected in step c in media, using stepwise increases in the concentration of a drug.

* * * * *

UNITED STATES PATENT AND TRADEMARK OFFICE
CERTIFICATE OF CORRECTION

PATENT NO. : 5,198,344
DATED : March 30, 1993
INVENTOR(S) : James M. Croop, Philippe Gros and David E. Housman It is certified that error appears in the above-indentified patent and that said Letters Patent is hereby corrected as shown below:

Column 16, line 63, delete "isolate" and insert --isolated--.

Column 17, line 21, after "and", delete " "after sequence", ".

Signed and Sealed this

Fourteenth Day of December, 1993

Attest:

BRUCE LEHMAN

Attesting Officer     Commissioner of Patents and Trademarks